US007355400B2

(12) United States Patent
Mikhaltsevitch et al.

(10) Patent No.: US 7,355,400 B2
(45) Date of Patent: Apr. 8, 2008

(54) PULSE SEQUENCES FOR EXCITING NUCLEAR QUADRUPOLE RESONANCE (75) Inventors: Vassili Timofeevitch Mikhaltsevitch, St. James (AU); Taras Nikolaevitch Rudakov, Willetton (AU); John Harold Flexman, Kardinya (AU); Peter Alaric Hayes, Wembly Downs (AU); Warrick Paul Chisholm, Ferndale (AU)

(73) Assignee: QRSciences Pty. Ltd., Australia, WA (US)

( * ) Notice: Subject to any disclaimer, the term of this patent is extended or adjusted under 35 U.S.C. 154(b) by 100 days.

(21) Appl. No.: 10/518,480

(22) PCT Filed: Jun. 20, 2003

(86) PCT No.: PCT/AU03/00777

§ 371 (c)(1),
(2), (4) Date: Sep. 29, 2005

(87) PCT Pub. No.: WO04/001453

PCT Pub. Date: Dec. 31, 2003

(65) Prior Publication Data

US 2006/0091883 A1    May 4, 2006

(30) Foreign Application Priority Data

Jun. 20, 2002    (AU) .................................... PS3077

(51) Int. Cl.
*G01V 3/00* (2006.01)
(52) U.S. Cl. ..................................... 324/300
(58) Field of Classification Search ................. 324/300
See application file for complete search history.

(56) References Cited

U.S. PATENT DOCUMENTS 5,233,300 A    8/1993    Buess et al.

(Continued)

FOREIGN PATENT DOCUMENTS

GB    2 200 462    8/1988

(Continued)

OTHER PUBLICATIONS

International Search Report dated Aug. 4, 2003.

(Continued)

*Primary Examiner*—Louis M. Arana
(74) *Attorney, Agent, or Firm*—Michael Bednarek; Paul, Hastings, Janofsky & Walker LLP (57) ABSTRACT

An apparatus and a method for producing a multi-pulse sequence for irradiating a substance provided with quadrupole nuclei with either integer or half-integer spins to detect an NQR signal emitted therefrom. The apparatus has pulse sequence generating means adapted to produce a combination of two or more pulse sequences, arranged so that a definite regularity of the phase alteration of pulses in each of the pulse sequences occurs that is equivalent to a shift of spectral components of the pulse sequences in relation to each other. Furthermore, in at least one of the pulse sequences, there are not less than two phases alternating. A preparatory pulse may be included in one of the pulse sequences to reduce the effect of temperature, increase the intensity of the NQR signal and simultaneously eliminate intensity anomalies. Alternatively, the combination of pulse sequences may be different from a combination of PAPS and NPAPS, and none of the pulse sequences contain a preparatory pulse.

15 Claims, 4 Drawing Sheets

U.S. PATENT DOCUMENTS

| | | | |
|---|---|---|---|
| 5,365,171 A | 11/1994 | Buess et al. | |
| 5,608,321 A | 3/1997 | Garroway et al. | |
| 6,194,898 B1 * | 2/2001 | Magnuson et al. | 324/300 |
| 6,208,136 B1 * | 3/2001 | Smith et al. | 324/300 |
| 6,392,408 B1 | 5/2002 | Barrall et al. | |
| 6,577,128 B1 | 6/2003 | Smith et al. | |

FOREIGN PATENT DOCUMENTS

| | | |
|---|---|---|
| GB | 2 255 414 | 11/1992 |
| GB | 2 338 787 | 12/1999 |
| RU | 1824559 | 6/1993 |
| RU | 1831680 | 7/1993 |
| WO | WO 92/17794 | 10/1992 |
| WO | WO 93/11441 | 6/1993 |
| WO | WO 96/26453 | 8/1996 |
| WO | WO 99/19740 | 4/1999 |

OTHER PUBLICATIONS

Flexman, et al., "The Detection of Explosives in Airport Luggage Using the Direct Nuclear Quadrupole Resonance Method," Detection of Bulk Explosives Advanced Techniques Against Terrorism, Proceedings of the NATO Advanced Research Workshop, held in St. Petersburg, Russia, Jun. 16-21, 2003, Series: NATO Science Series II: Mathematics, Physics and Chemistry, Schubert; Kuznetsov (Eds.) vol. 138, 2004, p. 113-124.

Garroway, et al., "Explosives Detection by Nuclear Quadrupole Resonance (NQR)," SPIE vol. 2276, 1994, pp. 139-149.

Garroway, et al., "Narcotics and Explosives Detection by 14N Pure NQR," SPIE vol. 2092, 1993, pp. 318-327.

Chen and Slichter, "Zero-Field NMR Study on a Spin-Glass: Iron-Doped 2H-Niobium Diselenide," Physical Review B, vol. 27, No. 1, Jan. 1, 1983, pp. 278-292.

Vega, et al., "Cu Nuclear Quadrupole Resonance of $YBa_2Cu_3O_x$ With Varying Oxygen Content," Physical Review B, vol. 39, No. 4, Feb. 1, 1989, pp. 2322-2332.

Kreis, et al., "Low Frequency Pulse Excitation in Zero Field Magnetic Resonance," J. Chem. Phys., vol. 89, No. 11, 1988, pp. 6623-6635.

Erickson, "Optically Detected Multipulse Nuclear-Quadrupole-Resonance Studies of Trivalent Praseodymium in Zero and Weak Static Magnetic Fields," Phyiscal Review B, vol. 39, No. 10, Apr. 1, 1989, pp. 6342-6347.

Singh and Armstrong, "Spin Thermodynamics Applied to Pure Nuclear Quadrupole Resonance for an Inhomogeneously Broadband Line in a Spin-3/2 System," Journal of Physics C: Solid State Physics, vol. 19, 1986, pp. L221-L227.

Bai, et al., "Zeeman-Perturbed Spin-Echo FT NQR Spectroscopy," Journal of Magnetic Resonance Series A, vol. 102, 1993, pp. 137-143.

Shastri, et al., "Distribution of Nonequivalent Aluminum Sites Revaled in Al-Cu-Ru and Al-Cu-Fe Quasicrystals by $^{27}Al$ NQR," Physical Review B, vol. 50, No. 6, Aug. 1, 1994, pp. 4224-4227.

Nickel and Kimmich, "2D Exchange NQR Spectroscopy," Journal of Molecular Structure, vol. 345, 1995, pp. 253-264.

Kohori, et al., "$^{27}Al$ NMR and NQR Studies of the Antiferromagnetic Superconductor $UPd_2Al_3$," Solid State Communications, vol. 95, No. 2, 1995, pp. 121-126.

Peterson and Oja, "A Pulsed Nuclear Quadrupole Resonance Spectrometer," Advances in Nuclear Quadrupole Resonance, vol. 1, ed. J.A.S. Smith (London: Heyden), 1974, pp. 179-184.

Ramachandran and Narasimhan, "A Coherent Nuclear Quadrupole Pulse and Double Resonance Spectrometer," Journal of Physics E: Scientific Instruments, vol. 16, 1983, pp. 643-648.

Harding, et al., "A Pulsed NQR-FFT Spectrometer for Nitrogen-14," Journal of Magnetic Resonance, vol. 36, 1979, pp. 21-33.

Hirschfeld and Klainer, "Short Range Remote NQR Measurements," Journal of Molecular Structure, vol. 58, 1980, pp. 63-77.

Grechishkin, "NQR Device for Detecting Plastic Explosives, Mines and Drugs," Applied Physics A, vol. 55, 1992, pp. 505-507.

Grechishkin and Sinyavskii, "Remote Nuclear Quadrupole Resonance in Solids," Physics, Uspekhi, vol. 38, No. 10, 1993, pp. 980-1003.

Grechishkin, "Application of Multipulse Sequences in Remote NQR," Applied Physics A, vol. 58, 1994, pp. 63-65.

Klainer, et al., "Fourier Transform Nuclear Quadrupole Resonance Spectroscopy," in "Fourier, Hadamard and Hilbert Transforms in Chemistry," A.G. Marshall, Ed. Plenum, New York, 1982, pp. 147-182.

Maricq, "Quasistationary State and its Decay to Equilibrium in the Pulsed Spin Locking of a Nuclear Quadrupole Resonance," Phyiscal Review B, vol. 33, No. 7, Apr. 1, 1986, pp. 4501-4513.

Alexander and Tzalmona, "Relaxation by Slow Motional Processes. Effect of Molecular Rotations in Pure Quadrupole Resonance," Physical Review, vol. 138, No. 3A, May 3, 1965, pp. A845-A855.

Carr, "Steady-State Free Precession of Nuclear Magnetic Resonance," Physical Review, vol. 112, No. 5, Dec. 1, 1958, pp. 1693-1701.

Osokin, et al., "The Quasistationary States in Multipulse NQR," Z. Naturforsch, vol. 47A, 1992, pp. 439-445.

Osokin and Shagalov, "NQR Transient Nutation and Rotary Echoes in the Effective Field of Multiple-Pulse Sequences," Solid State Nuclear Magnetic Resonance, vol. 10, 1997, pp. 63-72.

Liao and Zax, "Analysis of Signal-to-Noise Ratios for Noise Excitation of Quadrupole Nuclear Spins in Zero Field," Journal of Physical Chemistry, vol. 100, No. 5, 1996, pp. 1483-1487.

Marino and Klainer, "Multiple Spin Echoes in Pure Quadrupole Resonance," The Journal of Chemical Physics, vol. 67, No. 7, Oct. 1, 1997, pp. 3388-3389.

Hitrin, et al., Pulsed Spin Locking Theory in Pure Quadrupole Resonance, vol. 83, 1982, pp. 269-275.

Zussman, "Effect of Molecular Reorientation in Urea on the $^{14}N$ PNQR Linewidth and Relaxation Time," The Journal of Chemical Physics, vol. 58, No. 4, Feb. 15, 1973, pp. 1514-1522.

Bradford, et al., "A Steady-State Transient Technique in Nuclear Induction," Physical Review, vol. 84, No. 1, 1951, pp. 157-158.

* cited by examiner

PULSE SEQUENCES FOR EXCITING NUCLEAR QUADRUPOLE RESONANCE

FIELD OF THE INVENTION

The present invention relates to the practical use of the nuclear quadrupole resonance (NQR) phenomenon for identifying substances that contain quadrupole nuclei with either integer or half-integer spins, particularly for identifying explosive or narcotic substances.

The invention has particular utility in multi-pulse radio frequency (RF) excitation of quadrupole nuclei and to the subsequent measurement of the NQR signal emitted therefrom where changes in temperature can effect measurement.

Throughout the specification, unless the context requires otherwise, the word "comprise" or variations such as "comprises" or "comprising", will be understood to imply the inclusion of a stated integer or group of integers but not the exclusion of any other integer or group of integers.

The term "preparatory pulse" means both a separate preparatory pulse and a group of preparatory pulses.

The term "a group of preparatory pulses" means a group of pulses that precede a multi-pulse sequence distributed within time interval $\leq 3T_{1\rho}$ ($T_{1\rho}$ being the time of spin-lattice relaxation in a rotating coordinate system), during which the NQR signal, as a rule, is not measured.

The term "the body of the sequence" is used to signify that portion of a multi-pulse sequence that does not contain any preparatory pulses; the measurement of an NQR signal usually occurring when the "body of the sequence" is in action.

BACKGROUND ART

The following discussion of the background art is intended to facilitate an understanding of the present invention only. It should be appreciated that the discussion is not an acknowledgement or admission that any of the material referred to is or was part of the common general knowledge as at the priority date of the application.

For the purposes of pulsed NQR, any solid sample containing quadrupole nuclei can be characterised by three parameters: the spin-lattice relaxation time $T_1$, the spin-spin relaxation time $T_2$ and the time of the induction signal damping $T_2^*$.

From the point of view of practical use in NQR, and on the basis of the above parameters, multi-pulse sequences can be classified into the following general groups:

Group I:
    Sequences of single pulses, which can include multi-pulse sequences of any type, if intervals between the pulses in these sequences exceed the spin-lattice relaxation time $T_1$.

Group II:
    Sequences with intervals between pulses $\tau$ that are within the limits $T_2^* < \tau << T_1$.

All echo-sequences (sequences composed of a certain number of pulses which are organised in such a way that the NQR signal is formed not directly after the radio frequency irradiation pulse, but after a certain delay, necessary for refocussing the magnetic momentum of the sample nuclei) could also be regarded as belonging to this type of sequence, because in the optimal formation of the echo signal the condition $T_2^* < \tau < T_2$ generally holds true.

One of the main peculiarities of this type of sequence is its apability to saturate the quadrupolar spin system of the sample. This can be observed when a multi-pulse sequence of this type is used, as the chain of NQR signals measured in the observation windows between the pulses decays with a time constant $T_{1e}$, which is called the effective relaxation time and lies within the limits of $T_2 \leq T_{1e} < T_1$ (or, to be more precise, within the limits of $T_2 \leq T_{1e} < T_{1\rho}$, where $T_{1\rho}$ is the relaxation time in rotating frame, with the permanent condition of $T_{1\rho} < T_1$).

Group III:
    Stochastic Sequences.

Group IV:
    Multi-pulse sequences of the Steady State Free Precession (SSFP) type. Intervals between pulses in these sequences ($\tau$) fulfil the condition of $\tau < T_2^*$.

This type can include quite complex formations, containing not only SSFP sequences but also special techniques for destroying the SSFP state; this "destruction" can be achieved by including the magnetic field gradient pulses, by using composite pulses so as to form a special phase alternation of the RF carrier frequency, etc. The purpose of this "destruction" is to overcome one of the main drawbacks of SSFP sequences—intensity anomalies, which manifest themselves by the decreasing amplitude and the increasing rate of signal decay when the parameters of an irradiating sequence approach resonance conditions $$n \cdot \omega_{\it{eff}} = m \cdot \frac{\pi}{\tau},$$

where $\tau$ is the interval between pulses of the sequence, n and m are whole numbers, an effective field $\omega_{\it{eff}}$ substitutes the effect of the RF pulses and the resonance offset Group V:
    Complex types of multi-pulse sequences containing sub-sequences of two or more of the above types of multi-pulse sequences.

The fifth group does not have any individual physical characteristics that do not relate to at least one of the previous groups. Therefore, only aspects of the first four groups of sequences in the above classification will be considered further.

Group I

Advantages:
1. No intensity anomalies;
2. No saturation problem, and therefore no signal decay.

Disadvantages:
1. At long $T_1$ times the detection time of a sample can exceed any practically acceptable limits;
2. Single pulses can only create a free induction decay (FID) signal, entirely determined—as well as magneto-acoustic ringing, piezo-electric effects and the spurious signals of the resonance circuit of the NQR detector probe—by the pulse that generated it. The consequence of this is that the NQR signal measured when the standard means of damping spurious signals is used, is considerably weakened, and often disappears completely.

Because of these disadvantages the first group of sequences is of little benefit for practical use in NQR.

Group II

Advantages:
1. Possibility of generating echo-signals with parameters depending not only on the last pulse but also on the preceding pulses of the sequence which can be used to cancel spurious signals while keeping and sometimes even increasing the intensity of the NQR signal;
2. Possibility of generating echo-signals at times exceeding "dead time" of the receive system of the spectrometer;
3. Possibility of saturating the sample, which enables the measurement of the spurious signals together with the NQR signals, then spurious signals only, after which the latter can be subtracted.

Disadvantages:
1. Time available for accumulating the NQR signal is limited by the time constant $T_{1e} < T_1$;
2. Echo sequences (which is one of the main advantages of this group), are not particularly effective in detecting a number of substances that have a little or zero asymmetry parameter, as the amplitude of echo-signals decreases with the decrease of the asymmetry parameter.

Group III

Advantages:
1. No intensity anomalies;
2. Possibility of saturating the sample to enable subtraction of spurious signals. Saturation in this case is entirely determined by the flip angle of the pulses and the time of spin-lattice relaxation $T_1$;
3. The stochastic resonance requires lower peak power. The peak power can be tens and even hundreds of times lower than when using coherent pulses and still achieve similar sensitivity.

Disadvantages:
1. Stochastic sequences belong to saturating sequences; however the saturation of the spin system limits the time of the NQR signal accumulation, as is the case with Group II sequences, which is equivalent to a loss of sensitivity; stochastic sequences do not produce the same advantages that Group II sequences can offer using echo signals.
2. Using a stochastic sequence for saturating a sample does not give any advantages as compared with normal saturation methods that use coherent pulses, but is technically more complicated to realise.
3. Using stochastic sequences requires introducing a random delay in the timing of the radio frequency pulses, but there are cases where the timing between radio frequency pulses is relatively short and any delays introduced in the timing tend to greatly increase the spectrometer time required to obtain the desired time average spectral data.

The general conclusion about the use of stochastic sequences in NQR for identification of explosive and narcotic substances is that they are more technically complicated to produce and the achieved sensitivity as a rule does not exceed that of coherent sequences.

Group IV

Advantages:
1. it is possible to receive a continuous chain of signals if the requirement $$n \cdot \omega_{eff} \neq m \cdot \frac{\pi}{\tau}$$

is met, which ensures unlimited time for signal accumulation. Here, $\tau$ is the pulse spacing of the sequence, n and m are whole numbers, and $\omega_{eff}$ represents the effective field which substitutes the effect of the RF pulses and the resonance offset.
2. it is possible to receive an NQR signal phase that is different from the phase of irradiating pulses, which can be used for cancelling intensity anomalies, or for subtracting spurious signals;
3. Comparatively little RF power is required for detecting samples in large volumes.

Disadvantages:
1. Intensity anomalies;
2. Higher requirements due to the time of damping ringing and the time of equipment insensitivity at short $T_2^*$.
When the requirement $$n \cdot \omega_{eff} \neq m \cdot \frac{\pi}{\tau}$$

is met, the SSFP sequences allow achievement of a greater signal-to-noise ratio per unit of time than any other multi-pulse sequences used for exciting the quadrupole spin system.

However, complying with this requirement cannot be guaranteed in practice because the exact value of the resonance offset in most cases is unknown due to the fact that the exact temperature of the sample is not known either.

Thus the dependence of the signal intensity on the resonance offset when using the SSFP sequences is characterised by the existence of intensity anomalies and these intensity anomalies make the SSFP group sensitive to the changes in the resonance frequency of the quadrupole spin system during temperature changes.

In the solid state when irradiating sequence parameters approach the resonance conditions, intensity anomalies are manifested specifically by the reduction of the amplitude and increase in damping of the signal as indicated by the equation:

$$n \cdot \omega_{eff} = m \cdot \frac{\pi}{\tau}.,$$

If the temperature of a sample leads to the setting of frequency $\omega_Q$ of the quadrupole transition in the sample such that the resonance condition $$n \cdot \omega_{eff} = m \cdot \frac{\pi}{\tau}$$

is met, then the chain of the NQR signals decays with time constant $T_{1e}$, which is the function of the frequency offset, pulse interval and the flip angle. At short $T_1$ times ($T_{1e} < T_1$) the decay happens quickly, decreasing sharply the sensitivity of detection, which can result in a sharp decline in the signal intensity or even in the complete loss of information about the presence (or absence) of the sample in the examined volume.

For a number of substances, the temperature dependence of the resonance frequencies of quadrupolar nuclei is quite considerable. For example, for RDX at frequency $\nu_+ = 5.192$ MHz at temperatures close to room temperature, the change in $^{14}$N resonance frequency is −520 Hz/° K, for PETN at the $^{14}$N frequency $v_+$=890 kHz it is −160 Hz/° K, for KNO$_3$ at nitrogen-14 line $v_+$=567 kHz it is −140 Hz/° K etc.

The maximum sensitivity in most cases is achieved in practice when using SSFP sequences, whereby if the parameters are properly chosen, the biggest signal to noise ratio in unit time may be acheived.

The first SSFP sequence consisting of identical coherent RF pulses was used in research relating to Nuclear Magnetic Resonance (NMR) in 1951 and was later studied in great detail. Subsequently in 1965, this sequence was first used in NQR research for measuring the T$_1$ of the $^{14}$N resonance line in hexamethylene tetramine. Then a two-frequency version of this sequence was used to measure relaxation times in urea, which involved the simultaneous irradiation of the two $^{14}$N resonance transitions $v_+$ and $v_-$ with two SSFP sequences.

Later, a sequence with identical coherent RF pulses and a nonzero resonance offset was used. Back then, some combinations of SSFP sequences were used to solve the problem of intensity anomalies in detecting explosives by the NQR method.

The following method of suppressing intensity anomalies was suggested.

To irradiate the sample, the basic version of the SSFP sequences was used—a sequence of coherent equally spaced pulses with a flip angle φ and the repetition cycle τ: [τ/2–φ–τ/2]$_n$, where n is the number of the sequence cycles (it is also possible to write it down as [φ–τ]$_n$).

The irradiation was done with different series of pulses, with the carrier frequency of pulses in each series corresponding to one of the two values: f$_0$ and $$f_0 \pm \frac{2}{\tau},$$

where f$_0$ is the frequency close to the resonance frequency.

If there was no signal when irradiating with the series that had the carrier frequency f$_0$, the sample would then be irradiated with the other series with the carrier frequency $$f_0 \pm \frac{2}{\tau}.$$

The difference in the frequency of both carrier frequencies corresponds to the difference between the frequencies at which the maximum and the minimum signal intensity was observed.

It was then suggested to use combinations of sequences with phase alternating (PAPS) and without phase alternating (NPAPS): [φ$_x$–τ–φ$_x$–τ]$_n$[φ$_x$–τ–φ$_{-x}$–τ]$_n$, where the bottom index at the flip angle sign φ designates the phase of the carrier frequency for the RF pulse, and n is the number of cycles of the sequence.

In this case, if in the intervals corresponding to PAPS, the maximum signal was achieved, then in the intervals corresponding to NPAPS, the minimum signal would be observed. Such sequence combinations permitted irradiating the sample without switching the carrier frequency.

Essentially, two separate methods were proposed by which to perform the signal accumulation.

In the first method, the signals received after φ$_{-x}$ pulses of the PAPS sequence were subtracted from the signals received after φ$_x$ pulses of the NPAPS sequence, and those received after φ$_x$ of the PAPS sequence were added together with the resultant signal. This allowed not only a decrease in intensity anomalies, but also elimination of magneto-acoustic ringing.

In the second method, the signals received after φ$_x$ pulses of both PAPS and NPAPS sequences are added together, and the signals received after φ$_{-x}$ pulses are subtracted from the resultant signal.

The maximum accumulated signal achieved by using either method of accumulation is less than the maximum achieved when using only NPAPS or PAPS by $\sqrt{2}$ times.

Figure 1:
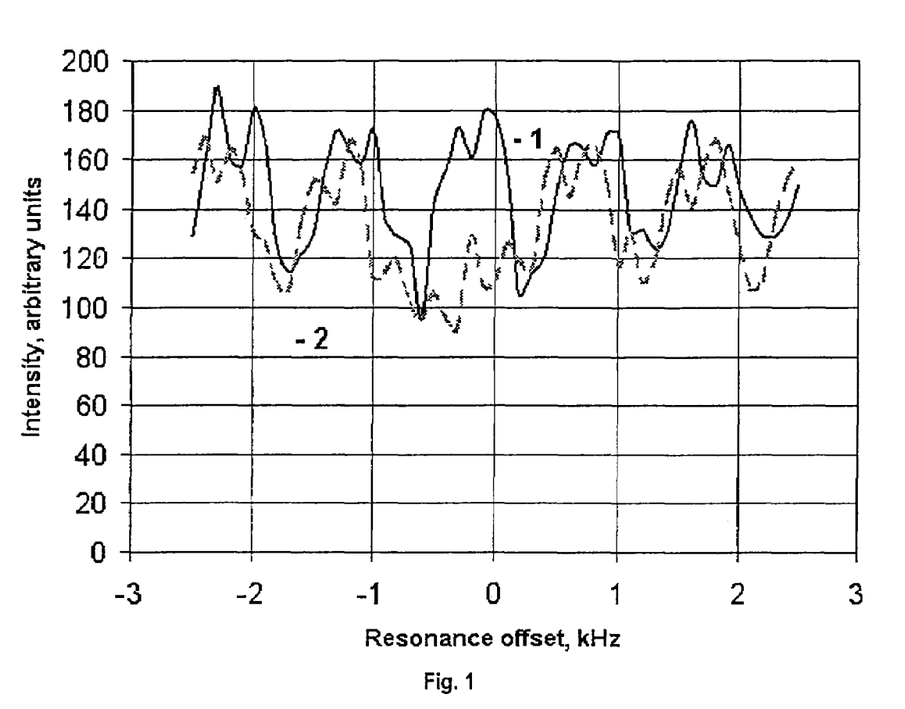
FIG. 1 is a graph representing curves corresponding to two dependencies of the intensity of NQR signals plotted against the resonance frequency offset in kHz, whereby the NQR signals are measured at the resonance frequency of $NaNO_2$, which is at the line $\nu_-=3.603$ MHz. During the NPAPS and PAPS sequences, the rules of addition are determined by the first method (curve 1) and the second method (curve 2) respectively, as described in the aforementioned discussion of background art.

For the sake of comparison, as shown in FIG. 1, the curves corresponding to two dependencies of NQR signal on the frequency received for NaNO$_2$ are shown, after irradiation with NPAPS and PAPS sequences using the accumulation rules determined by the first method described above (curve 1) and the second method (curve 2), respectively.

Thus all methods described above for eliminating temperature effects associated with intensity anomalies at a prescribed number of accumulations result in decreasing the intensity of the measured signal, as compared with the maximum signal intensity possible to measure arising from using only one of the SSFP sequences.

DISCLOSURE OF THE INVENTION

A principal object of the present invention is to increase the accuracy of detection in specimens of prescribed substances such as, but not limited to, certain explosives and narcotics compared with previously known methods of detecting same using NQR.

It is a preferred object of the invention to provide a multi-pulse sequence that reduces the effect of temperature and increases the NQR signal intensity in the detection of NQR signals emitted from such specimens.

In accordance with one aspect of the invention, there is provided an apparatus for producing a multi-pulse sequence of the kind described for irradiating a substance provided with quadrupole nuclei to detect an NQR signal emitted therefrom, the apparatus having pulse sequence generating means adapted to produce a combination of two or more steady state free precession pulse sequences, arranged so that a definite regularity of the phase alteration of pulses in each of the pulse sequences occurs that is equivalent to a shift of spectral components of the pulse sequences in relation to each other, and that in at least one of the pulse sequences, there are not less than two phases alternating.

According to another aspect of the invention, there is provided a method for detecting a class of substance containing quadrupolar nuclei in a sample using nuclear quadrupole resonance, including the following steps:

generating a combination of the steady state free precession pulse sequences, the pulse sequences consisting of pulses that contain phases of the carrier frequency chosen from a certain set of unmatched phases distributed within the interval from 0 to 2π radian, with every sequence different from the others either by the number of phases chosen from the set, or by the unmatched phase order inside the sequence; and irradiating the sample with said combination of the pulse sequences.

Preferably, the method includes alternating not less than two unmatched phases in at least one of the pulse sequences.

Preferably, the method includes detecting nuclear quadrupole resonance signals when the combination of the pulse sequences irradiates the sample; and combining all said nuclear quadrupole resonance signals to generate the resulting signal.

Preferably, the predetermined frequency of the pulse sequence is near to one of the NQR frequencies of the substances to be detected.

Alternatively, it is preferred to mitigate the effect of temperature by using a combination of two or more sequences different from a combination of PAPS and NPAPS, arranged so that a definite regularity of the phase alteration of pulses in each of the sequences is equivalent to a shift of spectral components of the sequences in relation to each other, and in at least one of the sequences not less than two phases are alternating and none of the sequences contains a preparatory pulse.

According to a preferred arrangement of this alternative of the invention, there is provided a method of detecting a class of explosive or narcotic substances containing quadrupolar nuclei in a sample using nuclear quadrupole resonance, including the following steps:

generating a combination of the steady state free precession pulse sequences without a preparatory pulse, using a combination of two or more sequences different from a combination of PAPS and NPAPS, the pulse sequences consisting of pulses that contain phases of the carrier frequency chosen from a certain set of unmatched phases distributed within the interval from 0 to $2\pi$ radian, with every sequence different from the others either by the number of phases chosen from the set, or by the sequence order inside the sequence; and irradiating the sample with the combination of the pulse sequences.

Preferably, the method includes detecting nuclear quadrupole resonance signals when the combination of the pulse sequences irradiates the sample; and combining all said nuclear quadrupole resonance signals to generate the resulting signal.

In accordance with a further aspect of the invention, the principal object of the invention is achieved by completing one measurement act using a combination that consists of at least two multi-pulse sequences having the same carrier frequency of the RF pulses, but different phase shifts between pulses in each sequence of the said combination.

This results in all the sequences of the combination having a different effective carrier frequency, and, consequently, the NQR signals obtained after each of the sequences having a different dependence on the frequency offset. If the NQR signals from different sequences are combined, then the resulting intensity of the signal has a significantly reduced dependence on the frequency bffset and, consequently, the effect of temperature.

In a preferred aspect of the invention, it is important also to consider that any spin system has a non-zero "phase memory" time. The phenomenon of "phase memory" manifests itself in the fact that a sudden momentary perturbation of the spin system influences its evolution for a certain period of time. This phenomenon can be used to change the dependence of the NQR signal on the frequency offset to reduce the effect of temperature. For this purpose preparatory pulses (or groups of preparatory pulses) may be used that are switched on before one or several sequences of the combination.

BRIEF DESCRIPTION OF THE DRAWINGS

The invention will be better understood in the light of the following description of two preferred embodiments thereof. The description is made with reference to the accompanying drawings, wherein:

$$\phi_{0\phi}-\tau-(\phi_x-t_{delay}-T_{acq(+x)}-\phi_{-x}-t_{delay}-T_{acq(-x)})_n;$$

FIG. 3 is another graph, similar to FIGS. 1 and 2, but showing an example of using PAPS and NPAPS sequences in accordance with the first embodiment with preparatory pulses at the frequency $\nu_-$ for $NaNO_2$, wherein:

Curve 1 corresponds to PAPS and NPAPS sequences with preparatory pulses:

$$\phi_{0x}-\tau-(\phi_x-t_{delay}-T_{acq(+x)}-\phi_{-x}-t_{delay}-T_{acq(-x)})_n, \text{ and}$$
$$\phi_{0y}-\tau-(\phi_x-t_{delay}-T_{acq(+x)})_{2n};$$

and curve 2 is the result of an experiment with these sequences with the same number of accumulations but without preparatory pulses, corresponding to the second method described in relation to the background art;

$$\phi_{0y}-\tau-(\phi_x-t_{delay}-T_{acq(+x)})_{4m};$$

$$\phi_{0x}-\tau-(\phi_x-t_{delay}-T_{acq(+x)}-\phi_{-x}-t_{delay}-T_{acq(-x)})_{2m};$$

$$(\phi_x-t_{delay}-T_{acq(+x)}-\phi_y-t_{delay}-T_{acq(+y)}-\phi_{-x}-t_{delay}-T_{acq(-x)}-\phi_{-i}-t_{delay}-T_{acq(-y)})_m;$$

$$(\phi_x-t_{delay}-T_{acq(+x)}-\phi_{-y}-t_{delay}-T_{acq(-y)}-t_{delay}-T_{acq(-x)}-\phi_y-t_{delay}-T_{acq(+y)})_m; \text{ and}$$

$$(\phi_x-t_{delay}-T_{acq}-\phi_y-t_{delay}-T_{acq}-\phi_{-x}-t_{delay}-T_{acq}-\phi_{-y}-t_{delay}-T_{acq})_m, \text{ and}$$

$$(\phi_x-t_{delay}-T_{acq}-\phi_{-y}-t_{delay}-T_{acq}-\phi_{-x}-t_{delay}-T_{acq}-\phi_y-t_{delay}-T_{acq})_m;$$

wherein the experiments were carried out using RDX at the frequency line $\nu_-=3.410$ MHz.

BEST MODE(S) FOR CARRYING OUT THE INVENTION

The best mode for carrying out the invention is concerned with using multi-pulse RF sequences to excite an NQR signal in a substance containing quadrupole nuclei with either integer or half-integer spins for the purposes of detecting such a signal.

The particular apparatus for producing pulse sequences of this kind comprises a pulse generator, the hardware design of which is known, and described in the applicant's corresponding International Patent Application PCT/AU00/01214 (WO 01/25809), which is incorporated herein by reference.

In order to generate a pulse sequence, firstly a pulse programmer is used to create a low voltage level pulse sequence. Such programmer is capable of generating a continuous sine wave of a desired frequency (eg; 0.89 or 5.2 MHz) and of any phase by using a Direct Digital Synthesizer (DDS) or any RF source. To create a pulse sequence, a gate is used to divide the continuous sine wave into small pulses. For example, the gate switches on for ~300 μs and off for ~300 μs, repeatedly thereby creating a sequence of pulses. The user of the pulse generator generates the pulse sequence via a computer program in the controlling computer. The computer program enables the user to input the frequency, phase, duration and separation of any pulses and allows the user to repeat any parts of the pulse sequence in a loop. The entire pulse sequence is contained in the program and then converted into binary and sent to the pulse programmer and stored in memory. The CPU of the pulse programmer then takes the machine code stored in memory and creates the pulse sequence by changing the frequency and phase of the DDS and providing instructions to the gate as to when to switch, thereby creating the pulses.

A simplified example of the program used to create a pulse sequence is outlined below:
Set Transmit Frequency: 0.89 MHz
Set Phase: 0 degrees
Gate Open
Wait 300 μs
Gate Closed (thus first pulse is created 300 μs long of phase 0 degrees)
Wait 300 μs
Set Transmit Frequency: 0.89 MHz
Set Phase: 90 degrees
For 1000 loops
 Gate Open
 Wait 300 μs
 Gate Closed
 Wait 300 μs
End of Loop
(thus 1000 additional pulses are created each 300 μs long and spaced 300 μs of a phase 90 degrees).

Secondly, each pulse sequence is transmitted to the coil via a high power amplifier (1→5 kW), which amplifies the low voltage signal created by the pulse programmer to a higher voltage level which is sufficient to stimulate the nitrogen 14 nuclei.

Pursuant to the invention, temperature effects on the ability to detect and measure the NQR signal may be reduced by using multiple pulse sequences in which "the bodies of sequences" contain RF pulses with various sets of the carrier frequency phases.

Accordingly, the best mode for carrying out the invention involves producing a combination of two or more pulse sequences, arranged so that a definite regularity of the phase alteration of RF pulses in each of the pulse sequences occurs, which is equivalent to a shift of the spectral components of the pulse sequences in relation to each other, and further, in at least one of the pulse sequences, there are not less than two phases alternating.

For the purposes of considering the aforementioned pulse sequence analytically, it should be noted that as the effective carrier frequency of the sequence does not depend on the absolute value of the RF pulses' phase, but only on the difference between phases of adjacent pulses divided by the time interval between these pulses, all phases are calculated from the phase of the first pulse of the body of the sequence, which, irrespective of its actual value, will always be considered to be zero.

To explain this further, a group consisting of N (N≧2) different phases, containing all the phases of one combination of multi-pulse sequences has the following phases:

$$\phi_1, \phi_2, \ldots \phi_i, \ldots \phi_N. \quad (1)$$

All phases $\phi_i$, i=1 ... N are within the interval from 0 to $2\pi$ radian, $\phi_i \neq \phi_j$ if i≠j and $\phi_1=0$.

In accordance with the invention, the body of each pulse sequence must contain pulse cycles (at least one), with the pulses of each cycle containing one of the following N! sets of the carrier frequency phases:

one set of phases being of the type:   $\phi1_1, \phi1_2, \ldots \phi1_i, \ldots \phi1_N$;

N set of phases being of the type:   $\phi2_1, \phi2_2, \ldots \phi2_i, \ldots \phi2_{N-1}$;

$\frac{N!}{(N-i)!i!}$ sets of phases being of the type:   $\phi i_1, \phi i_2, \ldots \phi i_i, \ldots \phi i_{N-i}$;

N sets of phases being of the type: $\phi N_1$.

Here each phase $\phi i_k$ (i, k=1, ... N) is one of a set of phases (1), with $\phi i_k \neq \phi i_m$, if k≠m. The set $\phi 1_k$ is equivalent to the set $\phi_k$.

If the bodies of all sequences used in one detection process for a sample contain the same set of phases, they must differ from each other by at least the order of alternation of the pulse phases.

One embodiment of the best mode for carrying out the present invention is concerned with improving the detection of substances having a relaxation time $T_1$ comparable with the time of the duration of the pulse sequence.

In this embodiment, a preparatory pulse is used in an SSFP sequence to improve the value of the NQR signal. To explain the influence of a preparatory pulse included in an SSFP sequence, the characteristics of this type of sequence will now be considered in detail.

The development of the spin system of a substance containing quadrupole nuclei with either integer and half-integer spins from the moment that multi-pulse irradiation of a specimen of the substance starts, undergoes three main stages:

(1) transient processes;

(2) quasi-stationary state;

(3) stationary state.

As a rule, transient processes decay at times $t \leq 3T_2$, and are replaced by a quasi-stationary state.

One of the characteristics of the quasi-stationary state as compared with the stationary state proper, which replaces it at times $\leq 3T_{1\rho}$ ($T_{1\rho}$ is the time of spin-lattice relaxation in the rotating frame), is the presence of the "phase memory" which manifests itself by the spin-system "remembering" the effect of a preparatory pulse. After the time $3T_{1\rho}$ the spin-system completely adopts the stationary state and on meeting the condition of $$n \cdot \omega_{eff} \neq m \cdot \frac{\pi}{\tau}$$

a different from zero NQR signal exists as long as it is needed.

The fact that the "phase memory" of the spin system is limited by the time interval being $\leq 3T_{1\rho}$, means that a "group of preparatory pulses" may be provided, as well as a single preparatory pulse.

The first specific embodiment of the best mode for carrying out the present invention involves producing the multi-pulse sequence of the best mode in an SSFP type sequence, including a "preparatory pulse" or a" group of preparatory pulses" in at least one of the pulse sequences and the use of the quasi-stationary state in the pulse sequence to "remember" the effect of the preparatory pulse. The preparatory pulse increases the intensity of the NQR signal and at the same time reduces the temperature effects in the detection of a prescribed substance containing quadrupole nuclei in a specimen of such.

Figure 2:
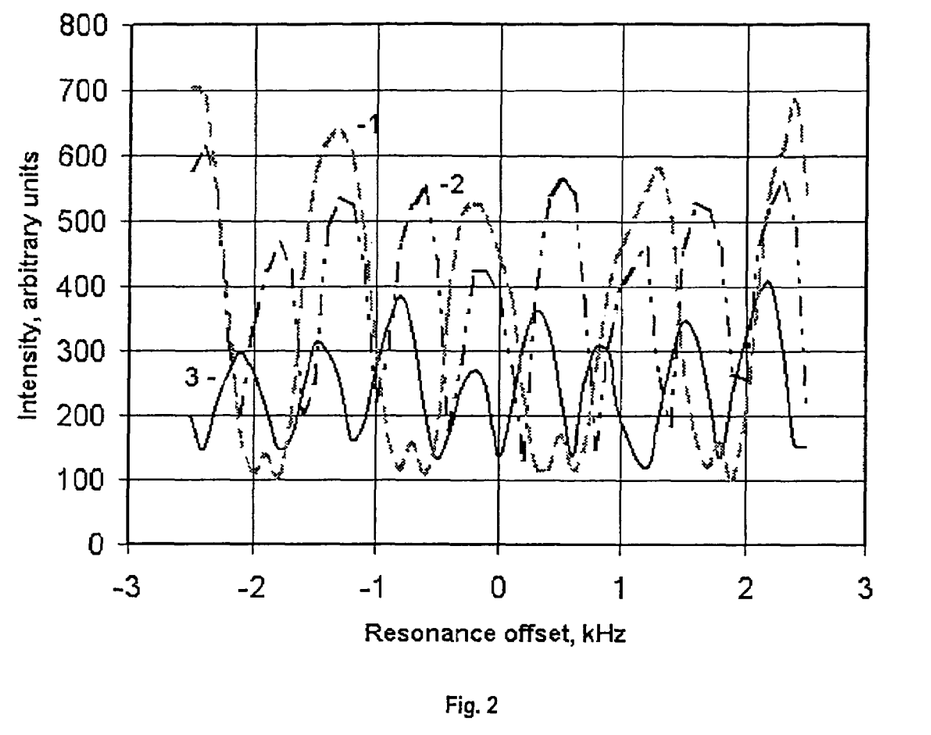
FIG. 2 is a graph similar to FIG. 1, but demonstrating examples of the effect of preparatory pulses on the value of the NQR signal in accordance with the first embodiment, where the preparatory pulses are switched on before the PAPS sequence.

FIG. 2 shows examples of the influence of preparatory pulses, used prior to the PAPS sequence $\phi_{0\phi}-\tau-(\phi_x-t_{delay}-T_{acq(+x)}-\phi_{-x}-t_{delay}-T_{acq(-x)})_n$, upon the value of the NQR signal detected in experiments carried out on a sample of NaNO$_2$, on line $\nu_-$. In all cases the experiments were carried out at room temperature.

The duration of the multi-pulse sequence in these examples is less than the spin-lattice relaxation time $T_1$. Here $\phi_0$ is the flip angle of the preparatory pulse; $\phi$ is the flip angle of the pulses of the sequence body; $\phi$ is the phase of the preparatory pulse; $t_{delay}$ is the time of the delay exceeding the "dead time" of the receiver system; $T_{acq(\Theta)}$ is acquisition time; $\Theta$ is the receiver phase.

Curve 1 was received at $\phi_0=\pi/2$ and $\phi=+x$, curve 2 was received without the preparatory pulse, and curve 3 was received at $\phi_0=\pi/2$ and $\phi=+y$.

Figure 3:
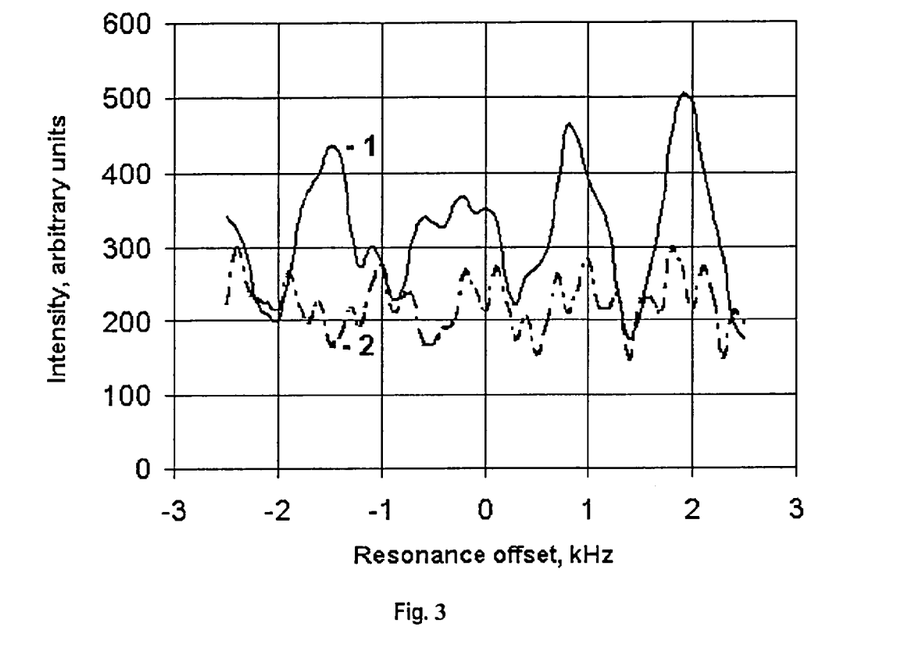
Figure 4:
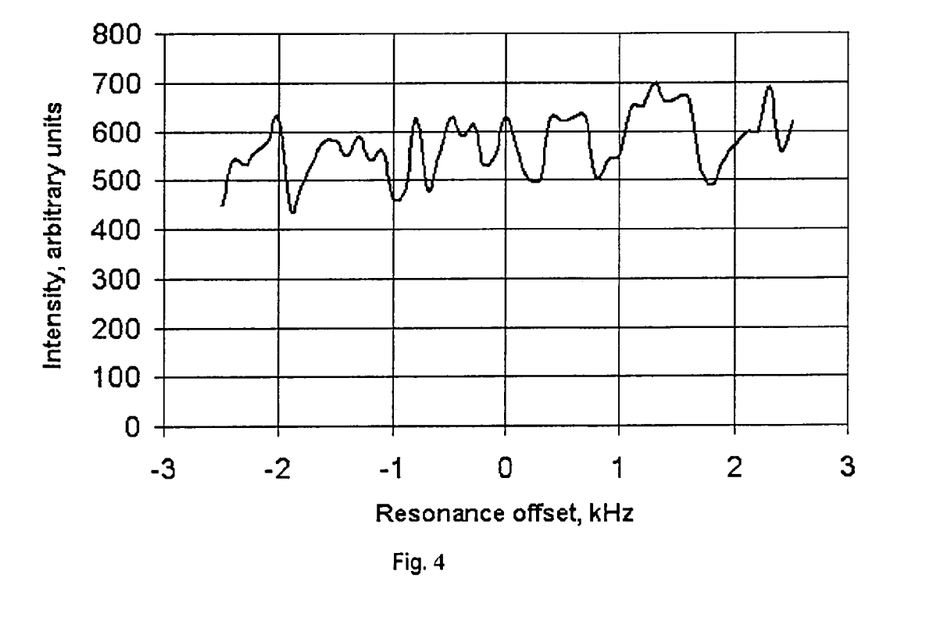
FIG. 4 is a graph similar to those of the preceding figures, but showing the result of using four sequences of the type for powdered RDX at the transition frequency $\nu_-=3.410$ MHz also in accordance with the first embodiment, the sequences being.

FIGS. 3 and 4 show two examples of the use of the first embodiment.

In both examples the magnetic field component $B_1$ of the RF pulses was 4.5 Gauss. The duration of the 90° pulse in the powder sample was 68 µs. Experiments were conducted on NaNO$_2$ at the frequency $\nu_-=3.603$ MHz at room temperature. The spin-lattice relaxation time for this line was $T_1=280$ ms.

FIG. 3 shows an example of using PAPS and NPAPS sequences with spin-lattice relaxation preparatory pulses. Curve 1 corresponds to the PAPS and NPAPS sequences with spin-lattice relaxation preparatory pulses, and curve 2 shows experimental results for the same sequences with the same number of accumulations but without the spin-lattice relaxation preparatory pulses (as in the second method described previously with respect to the background art).

The duration of each sequence was less than 170 ms, and the interval between the sequences was 2 s.

The parameters of the sequences NPAPS $\phi_{0y}-\tau-(\phi_x-t_{delay}-T_{acq(+x)})_{2n}$ and PAPS $\phi_{0x}-\tau-(\phi_x-t_{delay}-T_{acq(+x)}-\phi_{-x}-t_{delay}-T_{acq(-x)})_n$ are as follows:

$\phi_0=\phi=90°$; pulse duration $t_w=68$ µs; $\tau=778$ µs; $t_{delay}=600$ µs; $T_{acq(\Theta)}=1024$ µs; n=80.

Now adopting the designations: $T=t_w+t_{delay}+T_{acq(\Theta)}$; and where $f_0$ is the carrier frequency of the RF pulses, then the effective carrier frequencies $f_{eff}$ for both sequences would be $f_{eff} = f_0$ for NPAPS sequence;

$f_{eff} = f_0 + \frac{1}{2T}$ for PAPS sequence.

As can be seen from FIG. 3, the use of spin-lattice relaxation preparatory pulses does not allow an increase in the intensity of the NQR signal at the minimum points, but beyond the narrow areas, near the minimum, the signal intensity is considerably increased.

FIG. 4 shows the result of using four sequences for detecting powdered RDX, the sequences being of the following type:

$$\phi_{0y}-\tau-(\phi_x-t_{delay}-T_{acq(+x)})_{4m}; \quad (2)$$

$$\phi_{0x}-\tau-(\phi_x-t_{delay}-T_{acq(+x)}-\phi_{-x}-t_{delay}-T_{acq(-x)})_{2m}; \quad (3)$$

$$(\phi_x-t_{delay}-T_{acq(+x)}-\phi_y-t_{delay}-T_{acq(+y)}-\phi_{-x}-t_{delay}-T_{acq(-x)}-\phi_{-y}-t_{delay}-T_{acq(-y)})_m; \quad (4)$$

$$(\phi_x-t_{delay}-T_{acq(+x)}-\phi_{-y}-t_{delay}-T_{acq(-y)}-\phi_{-x}-t_{delay}-T_{acq(-x)}-\phi_y-t_{delay}-T_{acq(+y)})_m^*; \quad (5)$$

For all the four sequences m=50, the duration of delays, pulses and acquisition times coincides completely with the previous example. The intervals between sequences are also 2 s.

The effective carrier frequencies are as follows:

$f_{eff} = f_o$ for sequence (2);

$f_{eff} = f_o + \frac{1}{2T}$ for sequence (3);

$f_{eff} = f_o + \frac{1}{4T}$ for sequence (4);

$f_{eff} = f_o + \frac{1}{4T}$ for sequence (5).

Comparing FIGS. 3 and 4, it becomes obvious that intensity variations in the latter case are much weaker.

The second embodiment for carrying out the invention achieves a reduction in temperature effects by using a combination of two or more sequences other than PAPS and NPAPS, arranged so that a definite regularity of phase alternation of RF pulses in each of the sequences is equivalent to a shift of the spectrum components of the sequences in relation to each other. At least one of the sequences contains not less than two alternating phases and no sequences are arranged so that a definite regularity of the phase alteration of RF pulses in each of the sequences is equivalent to a shift of spectral components of the sequences in relation to each other. Further, in at least one of the sequences, there are not less than two phases that are alternating and none of the sequences contains a spin-lattice relaxation preparatory pulse or group of spin-lattice relaxation preparatory pulses.

This embodiment is intended for detecting substances with a relaxation time $T_1$ much shorter than the duration of the pulse sequence $T_{seq}$.

In the case when $T_1 \ll T_{seq}$, the time of "phase memory" is so short that using preparatory pulses will not necessarily produce an increase of the signal intensity, and the preparatory pulse can be omitted.

For reducing temperature effects the sequences must contain pulses with various sets of the carrier frequency phases.

As before, the phase of the first pulse of each sequence is taken to be zero irrespective of its actual value. The phases of all pulses of each sequence will be determined in relation to the phase of the first pulse of this sequence.

When using a set of N (N≥2) different phases $$\phi_1, \phi_2, \ldots \phi_i, \ldots \phi_N, \quad (6)$$

so that all phases are within the interval from 0 to $2\pi$ radian, If $\phi_i \neq \phi_j$ if i≠j, and $\phi_1=0$, the body of each pulse sequence must contain cycles of pulses (at least one), with the pulses of each cycle containing one of the following N! sets of carrier frequency phases:

one set of phases of the following type: $\phi 1_1, \phi 1_2, \ldots \phi 1_i, \ldots \phi 1_N$;

N sets of phases of the following type: $\phi 2_1, \phi 2_2, \ldots \phi 2_i, \ldots \phi 2_{N-1}$;

$\vdots$ $\dfrac{N!}{(N-i)!\, i!}$ sets of phases of the following type: $\phi i_1, \phi i_2, \ldots \phi i_i, \ldots \phi i_{N-i}$;

$\vdots$

N sets of phases of the following type: $\phi N_1$.

Here each phase $\phi i_k$ (i, k=1, ... N) is one of the phases of set (6), with $\phi i_k \neq \phi i_m$, if k≠m. Set $\phi 1_k$ is equivalent to set $\phi_k$.

If sequences from one combination used in one detection process contain the same pulse phase set, they must differ by at least the sequence order of the phase alternation.

Figure 5:
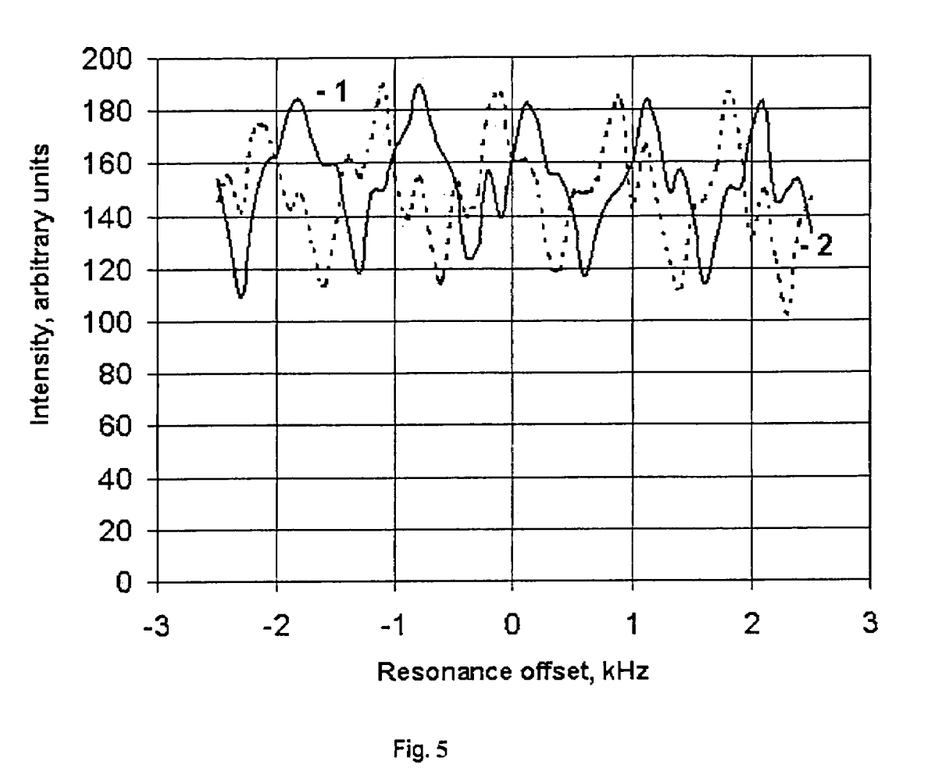
FIG. 5 is a graph similar to those of the preceding figures, but showing two examples of using a combination of sequences without preparatory pulses in accordance with the second embodiment, the sequences being.

Two examples of the use of the second embodiment are shown in FIG. 5.

Both examples present the use of a combination of sequences without preparatory pulses for powdered RDX.

$(\phi_x - t_{delay} - T_{acq} - \phi_y - t_{delay} - T_{acq} - \phi_{-x} - t_{delay} - T_{acq} - \phi_{-y} - t_{delay} - T_{acq})_m$ and $(\phi_x - t_{delay} - T_{acq} - \phi_{-y} - t_{delay} - T_{acq} - \phi_{-x} - t_{delay} - T_{acq} - \phi_y - t_{delay} - T_{acq})_m$.

Experiments were performed at the transition frequency $\nu_- = 3.410$ MHz at room temperature.

As in previous examples, the magnetic field component $B_1$ of the RF pulses equalled 4.5 Gauss. The spin-lattice relaxation time for this line was $T_1 = 11$ ms.

The difference between the two experiments shown in curves 1 and 2 in FIG. 5 consists only in the difference in the receive system phase.

Keeping in mind the phases of the receiver, the sequences corresponding to curve 1 can be presented as follows:

$(\phi_x - t_{delay} - T_{acq(+x)} - \phi_y - t_{delay} - T_{acq(+y)} - \phi_{-x} - t_{delay} - T_{acq(-x)} - \phi_{-y} - t_{delay} - T_{acq(-y)})_m;$ (7)

$(\phi_x - t_{delay} - T_{acq(+x)} - \phi_{-y} - t_{delay} - T_{acq(-y)} - \phi_{-x} - t_{delay} - T_{acq(-x)} - \phi_y - t_{delay} - T_{acq(+y)})_m.$ (8)

Curve 2 corresponds to the combination of the same sequences but in the second sequence the phase of the receiver is changed to the opposite:

$(\phi_x - t_{delay} - T_{acq(+x)} - \phi_y - t_{delay} - T_{acq(+y)} - \phi_{-x} - t_{delay} - T_{acq(-x)} - \phi_{-y} - t_{delay} - T_{acq(-y)})_m;$ (9)

$(\phi_x - t_{delay} - T_{acq(-x)} - \phi_{-y} - t_{delay} - T_{acq(+y)} - \phi_{-x} - t_{delay} - T_{acq(+x)} - \phi_y - t_{delay} - T_{acq(-y)})_m.$ (10)

For all the four sequences: m=50, $\phi=\pi/2$; the pulse duration $t_w=68$ μs; the delay after the pulse $t_{delay}=440$ μs; and the acquisition time $T_{acq(\theta)}=1024$ μs. The interval between sequences is two seconds.

The effective carrier frequencies equal:

$$f_{eff} = f_o + \frac{1}{4T}, \text{ for sequences (7), (9); and}$$

$$f_{eff} = f_o + \frac{3}{4T}, \text{ for sequences (8), (10).}$$

As a result of comparing curves 1 and 2, it is obvious that both combinations (7)-(8) and (9)-(10) show practically identical results with regards to reducing temperature effects, the only difference being an insignificant shift along the frequency axis.

It should be appreciated that the scope of the present invention is not limited to the specific embodiments described herein.

The invention claimed is:

1. A nuclear quadrupole resonance apparatus for detecting a substance containing nuclear quadrupole nuclei, comprising:
   a pulse sequence generator adapted to generate a combination of two or more steady state free precession pulse sequences, the steady state free precession pulse sequences having phases that alternate in a pattern to excite nuclear quadrupole nuclei in a frequency bandwidth which exceeds the frequency bandwidth covered by each of the steady state free precession pulse sequences individually to thereby minimize intensity variations caused by unknown temperature of the substance, wherein there are at least two different phases alternated in at least one of the pulse sequences;
   a detector to detect a nuclear quadrupole resonance signal generated from the substance under conditions of unknown temperature of the substance in response to the combination of steady state free precession pulse sequences, the detector being arranged to add the spectral components of the nuclear quadrupole resonance signals obtained from each of the steady state free precession pulse sequences of said combination; and
   a phase shifter to periodically shift the phases of the pulses of said steady state free precession pulse sequences according to a predetermined order.

2. An apparatus as claimed in claim 1, wherein at least one of said steady state free precession pulse sequences contains a preparatory pulse.

3. An apparatus as claimed in claim 1, wherein none of said steady state free precession pulse sequences contains a preparatory pulse.

4. An apparatus as claimed in claim 1, wherein the nuclear quadrupole resonance frequency of the sample exceeds the frequency bandwidth of each of the steady state free precession pulse sequences.

5. A method as claimed in claim 4, comprising generating a combination of steady state free precession pulse sequences wherein at least one of said steady state free precession pulse sequences has a preparatory pulse.

6. A method as claimed in claim 4, wherein a predetermined frequency of the steady state free precession pulse sequence is near to one of the nuclear quadrupole resonance frequencies of the substance to be detected.

7. A method as claimed in claim 4, comprising generating one or more combinations of steady state free precession pulse sequences without a preparatory pulse.

8. A method as claimed in claim 7, comprising generating a combination of steady state free precession pulse sequences wherein at least one of said steady state free precession sequences has a preparatory pulse.

9. A method as claimed in claim 7, wherein a predetermined frequency of the steady state free precession pulse sequence is near to one of the nuclear quadrupole resonance frequencies of the substance to be detected.

10. A method as claimed in claim 7, comprising generating one or more combinations of steady state free precession pulse sequences without a preparatory pulse.

11. A method as claimed in claim 4, wherein the nuclear quadrupole resonance frequency of the sample exceeds the frequency bandwidth of each of the steady state free precession pulse sequences.

12. A method of nuclear quadrupole resonance for detecting a substance containing nuclear quadrupole nuclei, the method comprising:
generating a combination of steady state free precession pulse sequences, the combination having phases of the carrier frequency of the pulses that are chosen from a predetermined set of phases distributed within the interval from 0 to 2 pi radian, each pulse sequence differing from other pulse sequences by either (i) the number of different phases chosen from the set, or (ii) the order of the phases inside the pulse sequence; wherein there at least two different phases alternated in at least one of the pulse sequences such that intensity variations caused by unknown temperature of the substance are minimized;
irradiating the sample with the combination of steady state free precession pulse sequences;
detecting a nuclear quadrupole resonance signal from the substance under conditions of unknown temperature of the substance in response to the combination of steady state free precession pulse sequences; and
adding the spectral components of the nuclear quadrupole resonance signals obtained from each of the steady state free precession pulse sequences of the combination.

13. A method of nuclear quadrupole resonance for detecting a substance containing nuclear quadrupole nuclei, the method comprising:
minimizing intensity variations caused by unknown temperature of the substance by generating a combination of steady state free precession pulse sequences, within which the phases of the pulses alternate in a pattern to excite nuclear quadrupole nuclei in a frequency bandwidth which exceeds the frequency bandwidth covered by each of the steady state free precession pulse sequences individually, wherein there are at least two different phases alternated in at least one of the steady state free precession pulse sequences;
irradiating the substance with the combination of steady state free precession pulse sequences;
detecting a nuclear quadrupole resonance signal generated from the substance under conditions of unknown temperature of the substance in response to the combination of steady state free precession pulse sequences; and
adding the spectral components of the nuclear quadrupole resonance signals obtained from each of the steady state free precession pulse sequences of the combination.

14. A nuclear quadrupole resonance apparatus for detecting a substance containing nuclear quadrupole nuclei, comprising:
pulse sequence generating means for generating a combination of two or more steady state free precession pulse sequences, in which the phases of the steady state free precession pulse sequences alternate in a pattern to excite nuclear quadrupole nuclei in a frequency bandwidth which exceeds the frequency bandwidth covered by each of the steady state free precession pulse sequences individually to thereby minimize intensity variations caused by unknown temperature of the substance, wherein there are at least two different phases alternated in at least one of the steady state free precession pulse sequences;
detector means for detecting a nuclear quadrupole resonance signal generated from the substance under conditions of unknown temperature of the substance in response to the combination of steady state free precession pulse sequences, the detector means being arranged to add the spectral components of the nuclear quadrupole resonance signals obtained from each of the steady state free precession pulse sequences of said combination; and
phase shifting means for periodically shifting the phases of the pulses of said steady state free precession pulse sequences according to a predetermined order.

15. A nuclear quadrupole resonance apparatus for detecting a substance containing nuclear quadrupole nuclei, comprising:
means for generating a combination of two or more steady state free precession pulse sequences, in which the phases of the steady state free precession pulse sequences alternate in a pattern to excite nuclear quadrupole nuclei in a frequency bandwidth which exceeds the frequency bandwidth covered by each of the steady state free precession pulse sequences individually to thereby minimize intensity variations caused by unknown temperature of the substance, wherein there are at least two different phases alternated in at least one of the steady state free precession pulse sequences;
detector means for detecting a nuclear quadrupole resonance signal generated from the substance under conditions of unknown temperature of the substance in response to the combination of steady state free precession pulse sequences, the detector means being arranged to add the spectral components of the nuclear quadrupole resonance signals obtained from each of the steady state free precession pulse sequences of the combination; and
phase shifting means for periodically shifting the phases of the pulses of said steady state free precession pulse sequences according to a predetermined order.

* * * * *